United States Patent
Yang et al.

(10) Patent No.: US 11,524,034 B2
(45) Date of Patent: Dec. 13, 2022

(54) CHIMERIC ANTIGEN RECEPTOR COMPRISING THIRD SIGNAL RECEPTOR AND USE THEREOF

(71) Applicant: SHANGHAI LONGYAO BIOTECHNOLOGY INC., LTD., Shanghai (CN)

(72) Inventors: Xuanming Yang, Shanghai (CN); Yangxin Fu, Shanghai (CN); Xin Wang, Shanghai (CN); Shengqin Ye, Shanghai (CN); Min Li, Shanghai (CN)

(73) Assignee: Shanghai Longyao Biotechnology Inc., Ltd., Shanghai (CN)

( * ) Notice: Subject to any disclaimer, the term of this patent is extended or adjusted under 35 U.S.C. 154(b) by 0 days.

(21) Appl. No.: 17/127,283

(22) Filed: Dec. 18, 2020

(65) Prior Publication Data

US 2021/0169933 A1 Jun. 10, 2021

Related U.S. Application Data

(63) Continuation of application No. PCT/CN2019/077923, filed on Mar. 13, 2019.

(30) Foreign Application Priority Data

Jun. 20, 2018 (CN) .......................... 201810636414.1

(51) Int. Cl.
*A61K 35/17* (2015.01)
*C07K 14/725* (2006.01)
*C07K 16/28* (2006.01)

(52) U.S. Cl.
CPC .......... *A61K 35/17* (2013.01); *C07K 14/7051* (2013.01); *C07K 16/2887* (2013.01); *C07K 16/28* (2013.01); *C07K 16/2851* (2013.01); *C07K 16/2863* (2013.01); *C07K 16/2869* (2013.01); *C07K 16/2878* (2013.01); *C07K 2317/622* (2013.01); *C07K 2319/03* (2013.01); *C07K 2319/033* (2013.01)

(58) Field of Classification Search
None
See application file for complete search history.

(56) References Cited

FOREIGN PATENT DOCUMENTS

| CN | 103582699 A | 2/2014 |
| CN | 105777911 A | 7/2016 |
| WO | 2017173256 A1 | 10/2017 |

OTHER PUBLICATIONS

Chen et al (Medical Science Monitor, 21:2110-2115, 2015).*
Hudecek et al. (Clin. Cancer Res. Jun. 15, 2013; 19 (12): 3153-64).*
Bridgeman et al. (J. Immunol. Jun. 15, 2010; 184 (12): 6938-49).*
PCT/CN2019/077923 International Search Report dated Jun. 17, 2019.

* cited by examiner

*Primary Examiner* — Patricia Duffy
(74) *Attorney, Agent, or Firm* — Honigman LLP; Thomas A. Wootton, Esq.; Jonathan P. O'Brien

(57) ABSTRACT

The present invention provides a chimeric antigen receptor having a structure of scFv(X)-(Y)CD 3zeta-MN.X comprises a tumor targeting antibody or a ligand or receptor capable of specifically binding to a tumor. Y is an intracellular region of a costimulatory receptor selected from ICOS, CD28, CD27, HVEM, LIGHT, CD40L, 4-1BB, OX40, DR3, GITR, CD30, SLAM, CD2, and CD226; M is an intracellular region of a gamma chain family cytokine receptor, the cytokine receptor being selected from IL2Ra, IL2Rb, IL4Ra, IL7Ra, IL9Ra, IL15Ra, and IL21Ra. N is an intracellular region of IL2Rg. The present invention further provides a CAR-T cell constructed from the recombinant expression vector of said chimeric antigen receptor, a preparation method therefor and the use thereof. The CAR-T cell of the present invention significantly improves tumor killing capacity and amplification capacity.

6 Claims, 11 Drawing Sheets

Specification includes a Sequence Listing.

SEQUENCE LISTING

<160> NUMBER OF SEQ ID NOS: 7

<210> SEQ ID NO 1
<211> LENGTH: 468
<212> TYPE: PRT
<213> ORGANISM: Artificial Sequence
<220> FEATURE:

<223> OTHER INFORMATION: the sequence of scFv-antihCD20-20BBZ

<400> SEQUENCE: 1

```
Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Val Ser Tyr Ile
            20                  25                  30
His Trp Phe Gln Gln Lys Pro Gly Ser Ser Pro Lys Pro Trp Ile Tyr
        35                  40                  45
Ala Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                85                  90                  95
Phe Gly Gly Gly Thr Lys Leu Glu Ile Lys Gly Gly Gly Ser Gly
            100                 105                 110
Gly Gly Gly Ser Gly Gly Gly Ser Gln Val Gln Leu Gln Gln Pro
        115                 120                 125
Gly Ala Glu Leu Val Lys Pro Gly Ala Ser Val Lys Met Ser Cys Lys
    130                 135                 140
Ala Ser Gly Tyr Thr Phe Thr Ser Tyr Asn Met His Trp Val Lys Gln
145                 150                 155                 160
Thr Pro Gly Arg Gly Leu Glu Trp Ile Gly Ala Ile Tyr Pro Gly Asn
                165                 170                 175
Gly Asp Thr Ser Tyr Asn Gln Lys Phe Lys Gly Lys Ala Thr Leu Thr
            180                 185                 190
Ala Asp Lys Ser Ser Ser Thr Ala Tyr Met Gln Leu Ser Ser Leu Thr
        195                 200                 205
Ser Glu Asp Ser Ala Val Tyr Tyr Cys Ala Arg Ser Thr Tyr Tyr Gly
    210                 215                 220
Gly Asp Trp Tyr Phe Asn Val Trp Gly Ala Gly Thr Thr Val Thr Val
225                 230                 235                 240
Ser Ala Ala Ala Thr Thr Thr Pro Ala Pro Arg Pro Pro Thr Pro
                245                 250                 255
Ala Pro Thr Ile Ala Ser Gln Pro Leu Ser Leu Arg Pro Glu Ala Cys
            260                 265                 270
Arg Pro Ala Ala Gly Gly Ala Val His Thr Arg Gly Leu Asp Phe Ala
        275                 280                 285
Cys Asp Ile Tyr Ile Trp Ala Pro Leu Ala Gly Thr Cys Gly Val Leu
    290                 295                 300
Leu Leu Ser Leu Val Ile Thr Leu Tyr Cys Lys Arg Gly Arg Lys Lys
305                 310                 315                 320
Leu Leu Tyr Ile Phe Lys Gln Pro Phe Met Arg Pro Val Gln Thr Thr
                325                 330                 335
Gln Glu Glu Asp Gly Cys Ser Cys Arg Phe Pro Glu Glu Glu Glu Gly
            340                 345                 350
Gly Cys Glu Leu Arg Val Lys Phe Ser Arg Ser Ala Asp Ala Pro Ala
        355                 360                 365
Tyr Gln Gln Gly Gln Asn Gln Leu Tyr Asn Glu Leu Asn Leu Gly Arg
    370                 375                 380
Arg Glu Glu Tyr Asp Val Leu Asp Lys Arg Arg Gly Arg Asp Pro Glu
385                 390                 395                 400
```

Met Gly Gly Lys Pro Arg Arg Lys Asn Pro Gln Glu Gly Leu Tyr Asn
            405                 410                 415

Glu Leu Gln Lys Asp Lys Met Ala Glu Ala Tyr Ser Glu Ile Gly Met
        420                 425                 430

Lys Gly Glu Arg Arg Arg Gly Lys Gly His Asp Gly Leu Tyr Gln Gly
    435                 440                 445

Leu Ser Thr Ala Thr Lys Asp Thr Tyr Asp Ala Leu His Met Gln Ala
450                 455                 460

Leu Pro Pro Arg
465

<210> SEQ ID NO 2
<211> LENGTH: 195
<212> TYPE: PRT
<213> ORGANISM: Artificial Sequence
<220> FEATURE:
<223> OTHER INFORMATION: the sequence of IL7Ra intracellular region

<400> SEQUENCE: 2

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
        115                 120                 125

Ser Gly Lys Asn Gly Pro His Val Tyr Gln Asp Leu Leu Leu Ser Leu
    130                 135                 140

Gly Thr Thr Asn Ser Thr Leu Pro Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195

<210> SEQ ID NO 3
<211> LENGTH: 286
<212> TYPE: PRT
<213> ORGANISM: Artificial Sequence
<220> FEATURE:
<223> OTHER INFORMATION: the sequence of IL2Rb intracellular region

<400> SEQUENCE: 3

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
          35                  40                  45

Ser Pro Gly Gly Leu Ala Pro Glu Ile Ser Pro Leu Glu Val Leu Glu
 50                  55                  60

Arg Asp Lys Val Thr Gln Leu Leu Leu Gln Gln Asp Lys Val Pro Glu
 65                  70                  75                  80

Pro Ala Ser Leu Ser Ser Asn His Ser Leu Thr Ser Cys Phe Thr Asn
                 85                  90                  95

Gln Gly Tyr Phe Phe Phe His Leu Pro Asp Ala Leu Glu Ile Glu Ala
            100                 105                 110

Cys Gln Val Tyr Phe Thr Tyr Asp Pro Tyr Ser Glu Asp Pro Asp
            115                 120                 125

Glu Gly Val Ala Gly Ala Pro Thr Gly Ser Ser Pro Gln Pro Leu Gln
    130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
            180                 185                 190

Ser Leu Gln Glu Arg Val Pro Arg Asp Trp Asp Pro Gln Pro Leu Gly
            195                 200                 205

Pro Pro Thr Pro Gly Val Pro Asp Leu Val Asp Phe Gln Pro Pro Pro
    210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
            260                 265                 270

Ser Leu Gln Glu Leu Gln Gly Gln Asp Pro Thr His Leu Val
            275                 280                 285

<210> SEQ ID NO 4
<211> LENGTH: 569
<212> TYPE: PRT
<213> ORGANISM: Artificial Sequence
<220> FEATURE:
<223> OTHER INFORMATION: the sequence of IL4Ra intracellular region

<400> SEQUENCE: 4

Lys Ile Lys Lys Glu Trp Trp Asp Gln Ile Pro Asn Pro Ala Arg Ser
1               5                   10                  15

Arg Leu Val Ala Ile Ile Ile Gln Asp Ala Gln Gly Ser Gln Trp Glu
            20                  25                  30

Lys Arg Ser Arg Gly Gln Glu Pro Ala Lys Cys Pro His Trp Lys Asn
        35                  40                  45

Cys Leu Thr Lys Leu Leu Pro Cys Phe Leu Glu His Asn Met Lys Arg
    50                  55                  60

Asp Glu Asp Pro His Lys Ala Ala Lys Glu Met Pro Phe Gln Gly Ser
65                  70                  75                  80

Gly Lys Ser Ala Trp Cys Pro Val Glu Ile Ser Lys Thr Val Leu Trp
                85                  90                  95

Pro Glu Ser Ile Ser Val Val Arg Cys Val Glu Leu Phe Glu Ala Pro
            100                 105                 110

Val Glu Cys Glu Glu Glu Glu Val Glu Glu Lys Gly Ser Phe
            115                 120                 125

Cys Ala Ser Pro Glu Ser Ser Arg Asp Asp Phe Gln Glu Gly Arg Glu
        130                 135                 140

Gly Ile Val Ala Arg Leu Thr Glu Ser Leu Phe Leu Asp Leu Leu Gly
145                 150                 155                 160

Glu Glu Asn Gly Gly Phe Cys Gln Gln Asp Met Gly Glu Ser Cys Leu
                165                 170                 175

Leu Pro Pro Ser Gly Ser Thr Ser Ala His Met Pro Trp Asp Glu Phe
            180                 185                 190

Pro Ser Ala Gly Pro Lys Glu Ala Pro Pro Trp Gly Lys Glu Gln Pro
        195                 200                 205

Leu His Leu Glu Pro Ser Pro Pro Ala Ser Pro Thr Gln Ser Pro Asp
        210                 215                 220

Asn Leu Thr Cys Thr Glu Thr Pro Leu Val Ile Ala Gly Asn Pro Ala
225                 230                 235                 240

Tyr Arg Ser Phe Ser Asn Ser Leu Ser Gln Ser Pro Cys Pro Arg Glu
                245                 250                 255

Leu Gly Pro Asp Pro Leu Leu Ala Arg His Leu Glu Glu Val Glu Pro
            260                 265                 270

Glu Met Pro Cys Val Pro Gln Leu Ser Glu Pro Thr Thr Val Pro Gln
        275                 280                 285

Pro Glu Pro Glu Thr Trp Glu Gln Ile Leu Arg Arg Asn Val Leu Gln
        290                 295                 300

His Gly Ala Ala Ala Pro Val Ser Ala Pro Thr Ser Gly Tyr Gln
305                 310                 315                 320

Glu Phe Val His Ala Val Glu Gln Gly Gly Thr Gln Ala Ser Ala Val
                325                 330                 335

Val Gly Leu Gly Pro Pro Gly Glu Ala Gly Tyr Lys Ala Phe Ser Ser
            340                 345                 350

Leu Leu Ala Ser Ser Ala Val Ser Pro Glu Lys Cys Gly Phe Gly Ala
        355                 360                 365

Ser Ser Gly Glu Glu Gly Tyr Lys Pro Phe Gln Asp Leu Ile Pro Gly
        370                 375                 380

Cys Pro Gly Asp Pro Ala Pro Val Pro Val Pro Leu Phe Thr Phe Gly
385                 390                 395                 400

Leu Asp Arg Glu Pro Pro Arg Ser Pro Gln Ser Ser His Leu Pro Ser
                405                 410                 415

Ser Ser Pro Glu His Leu Gly Leu Glu Pro Gly Glu Lys Val Glu Asp
            420                 425                 430

Met Pro Lys Pro Pro Leu Pro Gln Glu Gln Ala Thr Asp Pro Leu Val
        435                 440                 445

Asp Ser Leu Gly Ser Gly Ile Val Tyr Ser Ala Leu Thr Cys His Leu
450                 455                 460

Cys Gly His Leu Lys Gln Cys His Gly Gln Glu Asp Gly Gly Gln Thr
465                 470                 475                 480

Pro Val Met Ala Ser Pro Cys Cys Gly Cys Cys Cys Gly Asp Arg Ser
                485                 490                 495

Ser Pro Pro Thr Thr Pro Leu Arg Ala Pro Asp Pro Ser Pro Gly Gly
            500                 505                 510

Val Pro Leu Glu Ala Ser Leu Cys Pro Ala Ser Leu Ala Pro Ser Gly
        515                 520                 525

```
Ile Ser Glu Lys Ser Lys Ser Ser Ser Phe His Pro Ala Pro Gly
            530                 535                 540

Asn Ala Gln Ser Ser Gln Thr Pro Lys Ile Val Asn Phe Val Ser
545                 550                 555                 560

Val Gly Pro Thr Tyr Met Arg Val Ser
                565

<210> SEQ ID NO 5
<211> LENGTH: 230
<212> TYPE: PRT
<213> ORGANISM: Artificial Sequence
<220> FEATURE:
<223> OTHER INFORMATION: the  sequence of IL9Ra intracellular region

<400> SEQUENCE: 5

Lys Leu Ser Pro Arg Val Lys Arg Ile Phe Tyr Gln Asn Val Pro Ser
1               5                   10                  15

Pro Ala Met Phe Phe Gln Pro Leu Tyr Ser Val His Asn Gly Asn Phe
            20                  25                  30

Gln Thr Trp Met Gly Ala His Gly Ala Gly Val Leu Leu Ser Gln Asp
        35                  40                  45

Cys Ala Gly Thr Pro Gln Gly Ala Leu Glu Pro Cys Val Gln Glu Ala
    50                  55                  60

Thr Ala Leu Leu Thr Cys Gly Pro Ala Arg Pro Trp Lys Ser Val Ala
65                  70                  75                  80

Leu Glu Glu Glu Gln Glu Gly Pro Gly Thr Arg Leu Pro Gly Asn Leu
                85                  90                  95

Ser Ser Glu Asp Val Leu Pro Ala Gly Cys Thr Glu Trp Arg Val Gln
            100                 105                 110

Thr Leu Ala Tyr Leu Pro Gln Glu Asp Trp Ala Pro Thr Ser Leu Thr
        115                 120                 125

Arg Pro Ala Pro Pro Asp Ser Glu Gly Ser Arg Ser Ser Ser Ser Ser
    130                 135                 140

Ser Ser Ser Asn Asn Asn Asn Tyr Cys Ala Leu Gly Cys Tyr Gly Gly
145                 150                 155                 160

Trp His Leu Ser Ala Leu Pro Gly Asn Thr Gln Ser Ser Gly Pro Ile
                165                 170                 175

Pro Ala Leu Ala Cys Gly Leu Ser Cys Asp His Gln Gly Leu Glu Thr
            180                 185                 190

Gln Gln Gly Val Ala Trp Val Leu Ala Gly His Cys Gln Arg Pro Gly
        195                 200                 205

Leu His Glu Asp Leu Gln Gly Met Leu Leu Pro Ser Val Leu Ser Lys
    210                 215                 220

Ala Arg Ser Trp Thr Phe
225                 230

<210> SEQ ID NO 6
<211> LENGTH: 285
<212> TYPE: PRT
<213> ORGANISM: Artificial Sequence
<220> FEATURE:
<223> OTHER INFORMATION: the sequence of IL21Ra intracellular region

<400> SEQUENCE: 6

Ser Leu Lys Thr His Pro Leu Trp Arg Leu Trp Lys Lys Ile Trp Ala
1               5                   10                  15

Val Pro Ser Pro Glu Arg Phe Phe Met Pro Leu Tyr Lys Gly Cys Ser
            20                  25                  30
```

Gly Asp Phe Lys Lys Trp Val Gly Ala Pro Phe Thr Gly Ser Ser Leu
            35                  40                  45

Glu Leu Gly Pro Trp Ser Pro Glu Val Pro Ser Thr Leu Glu Val Tyr
 50                  55                  60

Ser Cys His Pro Pro Arg Ser Pro Ala Lys Arg Leu Gln Leu Thr Glu
 65                  70                  75                  80

Leu Gln Glu Pro Ala Glu Leu Val Glu Ser Asp Gly Val Pro Lys Pro
                85                  90                  95

Ser Phe Trp Pro Thr Ala Gln Asn Ser Gly Gly Ser Ala Tyr Ser Glu
                100                 105                 110

Glu Arg Asp Arg Pro Tyr Gly Leu Val Ser Ile Asp Thr Val Thr Val
            115                 120                 125

Leu Asp Ala Glu Gly Pro Cys Thr Trp Pro Cys Ser Cys Glu Asp Asp
130                 135                 140

Gly Tyr Pro Ala Leu Asp Leu Asp Ala Gly Leu Glu Pro Ser Pro Gly
145                 150                 155                 160

Leu Glu Asp Pro Leu Leu Asp Ala Gly Thr Thr Val Leu Ser Cys Gly
                165                 170                 175

Cys Val Ser Ala Gly Ser Pro Gly Leu Gly Gly Pro Leu Gly Ser Leu
            180                 185                 190

Leu Asp Arg Leu Lys Pro Pro Leu Ala Asp Gly Glu Asp Trp Ala Gly
            195                 200                 205

Gly Leu Pro Trp Gly Gly Arg Ser Pro Gly Gly Val Ser Glu Ser Glu
            210                 215                 220

Ala Gly Ser Pro Leu Ala Gly Leu Asp Met Asp Thr Phe Asp Ser Gly
225                 230                 235                 240

Phe Val Gly Ser Asp Cys Ser Ser Pro Val Glu Cys Asp Phe Thr Ser
                245                 250                 255

Pro Gly Asp Glu Gly Pro Pro Arg Ser Tyr Leu Arg Gln Trp Val Val
                260                 265                 270

Ile Pro Pro Pro Leu Ser Ser Pro Gly Pro Gln Ala Ser
            275                 280                 285

<210> SEQ ID NO 7
<211> LENGTH: 86
<212> TYPE: PRT
<213> ORGANISM: Artificial Sequence
<220> FEATURE:
<223> OTHER INFORMATION: the sequence of IL2Rg intracellular region

<400> SEQUENCE: 7

Glu Arg Thr Met Pro Arg Ile Pro Thr Leu Lys Asn Leu Glu Asp Leu
 1                   5                  10                  15

Val Thr Glu Tyr His Gly Asn Phe Ser Ala Trp Ser Gly Val Ser Lys
             20                  25                  30

Gly Leu Ala Glu Ser Leu Gln Pro Asp Tyr Ser Glu Arg Leu Cys Leu
            35                  40                  45

Val Ser Glu Ile Pro Pro Lys Gly Gly Ala Leu Gly Glu Gly Pro Gly
 50                  55                  60

Ala Ser Pro Cys Asn Gln His Ser Pro Tyr Trp Ala Pro Pro Cys Tyr
 65                  70                  75                  80

Thr Leu Lys Pro Glu Thr
                85

CHIMERIC ANTIGEN RECEPTOR COMPRISING THIRD SIGNAL RECEPTOR AND USE THEREOF

CROSS-REFERENCE TO RELATED APPLICATIONS

This application is a Continuation of and claims priority under 35 U.S.C. § 111 to Patent Cooperation Treaty application PCT/CN2019/077923, filed Mar. 13, 2019, which claims the benefit of Chinese Patent Application No. 201810636414.1, filed Jun. 20, 2018, priority is claimed to both of these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020-12-18_262790-481981_ST25.txt" is 19,333 bytes in size and was created on Dec. 18, 2020, and filed electronically herewith.

TECHNICAL FIELD

The present invention relates to the field of cellular immunotherapy, especially to a chimeric antigen receptor comprising a third signal receptor and use thereof.

BACKGROUND OF THE INVENTION

The use of immunological therapy for overcoming tumors has always been an important direction in the application of immunology in translational medicine. With the development of various omics (genomics, proteomics, etc.), tumor cells have been widely recognized due to their immunogenicity caused by mutations, which lays a theoretical foundation for tumor immunotherapy. At the same time, with the accumulation of tumor immunology research itself, tumor immunotherapy has recently made a great progress, and a series of new immunotherapy methods have gradually entered into the clinic. The current tumor immunology research has established the central position of T cell killing in tumor immunotherapy, and the chimeric antigen receptor T cell (CAR-T cell) is a tumor-killing cell which has combined the targeted recognition of antibody and the tumor-killing function of T cell, and generated by artificial modification.

The concept of chimeric antigen receptor T cell was first proposed by Gross, Waks and Eshhar in 1989. They expressed TNP-recognizing antibodies on T cells, achieving the antigen-specific, non-MHC-restricted activation of T cell and enhancement of effect, and proposed the concept of applying the CAR-T technology in tumor treatment. According to this principle, tumor-specific antibodies are embedded into T cells, which will give T cells new tumor-killing capabilities. After that, the CAR-T technology was introduced into anti-tumor clinical trials, but early CAR-T cells are not ideal in final clinical results since their intracellular signaling domain contains only the first signal, and the selected tumor type is a solid tumor. In 2008, the Fred Hutchison Cancer Institute and other institutions used CAR-T to treat B cell lymphoma, although the treatment results were not ideal, the key to this clinical trial is to confirm that the CAR-T treatment with CD20-expressing B cells as the target is relatively safe. Subsequently, in 2010, NCI reported a case of successful treatment of B cell lymphoma, using CAR-T targeting CD19, the patient's lymphoma was controlled, normal B cells were also eliminated, and serum Ig was significantly reduced, providing a theoretical and practical support for the effectiveness of CAR-T in the treatment of B cell-derived lymphomas. In 2011, a team led by Dr. Carl June of the University of Pennsylvania in the United States used CAR-T that specifically recognizes CD19 for the treatment of chronic lymphocytic leukemia derived from B cells, showing a "cure" effect. Clinical trials have been launched in relapsed and refractory acute lymphoblastic cell leukemia, and good results have also been achieved. Due to this breakthrough progress and the development of other immune regulation methods, Science magazine ranked tumor immunotherapy as the number one scientific and technological breakthrough in 2013. This success has caused widespread influence in countries around the world, and countries have begun to carry out a large number of CAR-T-based scientific research and clinical trials of tumor treatment.

The structure of CAR consists of an extracellular antigen recognition domain, an extracellular hinge region, a transmembrane domain, and an intracellular signal transduction domain. The extracellular antigen recognition domain consists commonly of a single-chain antibody, which specifically recognizes a tumor cell membrane surface molecule, or can be a ligand or a receptor of certain tumor-specific antigens. The extracellular hinge region is a spatial structure that separates the antigen recognition domain from the transmembrane domain, and its purpose is to provide a suitable spatial position, so that the extracellular antigen recognition domain can maintain the correct structure and transmit the intracellular signals before and after recognizing the antigen. The transmembrane domain is a structural domain for ensuring the positioning of the CAR molecule on the membrane surface. The intracellular signal transduction domain is a key part of mediating the CAR signal transduction, and is usually a combination of one or several first signals (for the recognition of TCR and WIC-I-peptide complex) and second signals (for the recognition of costimulatory receptor and costimulatory ligand). The first-generation CAR contains only the first signal, the second-generation CAR has one first signal and one second signal, and the third-generation CAR has one first signal and two second signal domains. Although CAR-T has achieved a great success in the treatment of leukemia derived from B cell, its relatively high recurrence rate and low effectiveness for solid tumors are great challenges currently. Therefore, there is an urgent clinic need of developing a new generation of high-efficiency CAR-T currently. In addition to the third-generation CAR-T, there are currently other new CAR-T design strategies, that is, introducing new regulatory molecules independent of CAR on the basis of the second-generation CAR-T to further enhance the function of CAR-T.

The application of CAR-T targeting the B cell surface targeting molecules CD19 and CD20 prepared from the patient's own blood cells in the treatment of B cell leukemia has been relatively mature, but there are a large number of recurrences, even if the response rate is high. In addition, the treatment efficiency for solid lymphoma is relatively low, which is related to the immunosuppressive microenvironment in solid tumors.

In solid tumors, there are a variety of immune cells, tumor cells and stromal cells, which together constitute the tumor microenvironment. The tumor microenvironment is usually immunosuppressive, and can inhibit endogenous anti-tumor T cell responses or adoptive T cells (such as CAR-T) at multiple levels, for example, leading to exhaustion of T cells and loss of tumor killing function, and eventually leading to the clearance of T cells. How to enhance the activation ability of CAR-T in solid tumors so that it can fight against the immune suppression in the tumor microenvironment is an important idea and direction for expanding CAR-T to solid tumor treatment.

However, the current CAR-T domains in clinical use still have insufficient tumor killing and expansion abilities, and have poor efficacy in controlling solid tumors/metastasis. Some CAR-T uses novel regulatory molecules such as IL-12, 4-1BBL, etc. These molecules will also produce non-specific activation effects on other non-CAR-T cells in addition to affecting the CAR-T, which may cause potential immune side effects.

SUMMARY OF THE INVENTION

An object of the present invention is to address the defects in the prior art, provide a chimeric antigen receptor including a third signal receptor and use thereof, and provide a CAR-T cell constructed by a recombinant expression vector of the chimeric antigen receptor, and in the CAR-T cell, the activation of T cells is regulated by a first signal (for recognizing of the TCR and MHC-I-peptide complex), a second signal (for recognizing of co-stimulating receptor and co-stimulating ligand) and a third signal (for recognizing of cytokine receptor and cytokine), which synergistically achieve massive expansion of T cells, exert effector functions, and eliminate infection or tumors.

To achieve the aforesaid object, the present invention utilizes the following technical solutions:

a first purpose of the present invention is to provide a chimeric antigen receptor including a third signal receptor, said chimeric antigen receptor has a structure of scFv(X)-(Y)CD3 zeta-MN;

wherein, X comprises a tumor-targeting antibody or a ligand or receptor capable of binding to a tumor; Y is an intracellular domain of a costimulatory receptor, said costimulatory receptor is selected from ICOS, CD28, CD27, HVEM, LIGHT, CD40L, 4-1BB, OX40, DR3, GITR, CD30, TIM1, SLAM, CD2, CD226; M is an intracellular domain of a gamma chain family cytokine receptor, said cytokine receptor is selected from IL2Ra, IL2Rb, IL4Ra, IL7Ra, IL9Ra, IL15Ra, IL21Ra; and N is an intracellular domain of IL2Rg.

For further optimizing the aforesaid chimeric antigen receptor, the technical means utilized by the present invention further includes:

further, said X is selected from anti-CD19 antibody, anti-CD20 antibody, EGFR antibody, HER2 antibody, EGFRVIII antibody, anti-PSMA antibody, anti-BCMA antibody, anti-CD22 antibody, anti-CD30 antibody. Understandably, X can also be other protein capable of specifically binding a tumor.

Further, said X is an anti-CD20 antibody, said Y is an intracellular domain of 4-1BB, said M is one selected from intracellular domain of IL2Rb, intracellular domain of IL4Ra, intracellular domain of IL7Ra, intracellular domain of IL9Ra, and intracellular domain of IL21Ra.

Further, said scFv(X)-(Y)CD3zeta is scFv-antihCD20-20BBZ with a sequence as set forth in SEQ ID No.1; the sequence of said intracellular domain of IL7Ra is as set forth in SEQ ID No.2; the sequence of said intracellular domain of IL2Rb is as set forth in SEQ ID No.3; the sequence of said intracellular domain of IL4Ra is as set forth in SEQ ID No.4;

the sequence of said intracellular domain of IL9Ra is as set forth in SEQ ID No.5; the sequence of said intracellular domain of IL21Ra is as set forth in SEQ ID No.6; and the sequence of said intracellular domain of IL2Rg is as set forth in SEQ ID No.7.

Wherein, each aforesaid sequence is specifically as follows:

SEQ ID No. 1:
QIVLSQSPAILSASPGEKVTMTCRASSSVSYIHWFQQKPGSSPK

PWIYATSNLASGVPVRFSGSGSGTSYSLTISRVEAEDAATYYCQ

QWTSNPPTFGGGTKLEIKGGGGSGGGGSGGGGSQVQLQQPGAEL

VKPGASVKMSCKASGYTFTSYNMHWVKQTPGRGLEWIGAIYPGN

GDTSYNQKFKGKATLTADKSSSTAYMQLSSLTSEDSAVYYCARS

TYYGGDWYFNVWGAGTTVTVSAAAATTTPAPRPPTPAPTIASQP

LSLRPEACRPAAGGAVHTRGLDFACDIYIWAPLAGTCGVLLLSL

VITLYCKRGRKKLLYIFKQPFMRPVQTTQEEDGCSCRFPEEEEG

GCELRVKFSRSADAPAYQQGQNQLYNELNLGRREEYDVLDKRRG

RDPEMGGKPRRKNPQEGLYNELQKDKMAEAYSEIGMKGERRRGK

GHDGLYQGLSTATKDTYDALHMQALPPR;

SEQ ID No. 2:
KKRIKPIVWPSLPDHKKTLEHLCKKPRKNLNVSFNPESFLDCQI

HRVDDIQARDEVEGFLQDTFPQQLEESEKQRLGGDVQSPNCPSE

DVVITPESFGRDSSLTCLAGNVSACDAPILSSSRSLDCRESGKN

GPHVYQDLLLSLGTTNSTLPPPFSLQSGILTLNPVAQGQPILTS

LGSNQEEAYVTMSSFYQNQ;

SEQ ID No. 3:
NCRNTGPWLKKVLKCNTPDPSKFFSQLSSEHGGDVQKWLSSPFP

SSSFSPGGLAPEISPLEVLERDKVTQLLLQQDKVPEPASLSSNH

SLTSCFTNQGYFFFHLPDALEIEACQVYFTYDPYSEEDPDEGVA

GAPTGSSPQPLQPLSGEDDAYCTFPSRDDLLLFSPSLLGGPSPP

STAPGGSGAGEERMPPSLQERVPRDWDPQPLGPPTPGVPDLVDF

QPPPELVLREAGEEVPDAGPREGVSFPWSRPPGQGEFRALNARL

PLNTDAYLSLQELQGQDPTHLV;

SEQ ID No. 4:
KIKKEWWDQIPNPARSRLVAIIIQDAQGSQWEKRSRGQEPAKCP

HWKNCLTKLLPCFLEHNMKRDEDPHKAAKEMPFQGSGKSAWCPV

EISKTVLWPESISWRCVELFEAPVECEEEEEVEEEKGSFCASPE

SSRDDFQEGREGIVARLTESLFLDLLGEENGGFCQQDMGESCLL

PPSGSTSAHMPWDEFPSAGPKEAPPWGKEQPLHLEPSPPASPTQ

SPDNLTCTETPLVIAGNPAYRSFSNSLSQSPCPRELGPDPLLAR

HLEEVEPEMPCVPQLSEPTTVPQPEPETWEQILRRNVLQHGAAA

APVSAPTSGYQEFVHAVEQGGTQASAVVGLGPPGEAGYKAFSSL

LASSAVSPEKCGFGASSGEEGYKPFQDLIPGCPGDPAPVPVPLF

TFGLDREPPRSPQSSHLPSSSPEHLGLEPGEKVEDMPKPPLPQE

QATDPLVDSLGSGIVYSALTCHLCGHLKQCHGQEDGGQTPVMAS

-continued

```
PCCGCCCGDRSSPPTTPLRAPDPSPGGVPLEASLCPASLAPSGI

SEKSKSSSSFHPAPGNAQSSSQTPKIVNFVSVGPTYMRVS;

SEQ ID No. 5:
KLSPRVKRIFYQNVPSPAMFFQPLYSVHNGNFQTWMGAHGAGVL

LSQDCAGTPQGALEPCVQEATALLTCGPARPWKSVALEEEQEGP

GTRLPGNLSSEDVLPAGCTEWRVQTLAYLPQEDWAPTSLTRPAP

PDSEGSRSSSSSSSSNNNNYCALGCYGGWHLSALPGNTQSSGPI

PALACGLSCDHQGLETQQGVAWVLAGHCQRPGLHEDLQGMLLPS

VLSKARSWTF;

SEQ ID No. 6:
SLKTHPLWRLWKKIWAVPSPERFFMPLYKGCSGDFKKWVGAPFT

GSSLELGPWSPEVPSTLEVYSCHPPRSPAKRLQLTELQEPAELV

ESDGVPKPSFWPTAQNSGGSAYSEERDRPYGLVSIDTVTVLDAE

GPCTWPCSCEDDGYPALDLDAGLEPSPGLEDPLLDAGTTVLSCG

CVSAGSPGLGGPLGSLLDRLKPPLADGEDWAGGLPWGGRSPGGV

SESEAGSPLAGLDMDTFDSGFVGSDCSSPVECDFTSPGDEGPPR

SYLRQWVVIPPPLSSPGPQAS;

SEQ ID No. 7:
ERTMPRIPTLKNLEDLVTEYHGNFSAWSGVSKGLAESLQPDYSE

RLCLVSEIPPKGGALGEGPGASPCNQHSPYWAPPCYTLKPET
```

Further, said extracellular hinge region of the chimeric antigen receptor is a region selected from CD8a or IgG; and said transmembrane domain of the chimeric antigen receptor is one selected from CD8a, CD28, CD137 or CD3.

A second object of the present invention is to provide a recombinant expression vector of any one of the aforesaid chimeric antigen receptor.

A third object of the present invention is to provide a CAR-T cell constructed with a recombinant expression vector of any one of the aforesaid chimeric antigen receptor.

A fourth object of the present invention is to provide a method of preparing the aforesaid CAR-T cell including the following steps:

step 1: construction of lentiviral vector and production of virus;

forming a fusion protein of scFv(X)-(Y)CD3zeta, M and N, and adding a lentiviral vector to both ends of the fusion protein, which is co-transfected with lentiviral packaging plasmid to obtain an scFv(X)-(Y)CD3zeta-MN virus;

step 2: preparation of scFv(X)-(Y)CD3zeta-MN CAR-T cell;

isolating a human PBMC for purification, culturing, infecting with the scFv(X)-(Y)CD3zeta-MN virus obtained in Step 1, and subjecting to cell expansion under suitable conditions to prepare scFv(X)-(Y)CD3zeta-MN CAR-T cells.

wherein X is a tumor-targeting antibody or other protein; Y is the intracellular domain of costimulatory receptor selected from ICOS, CD28, CD27, HVEM, LIGHT, CD40L, 4-1BB, OX40, DR3, GITR, CD30, TIM1, SLAM, CD2, CD226; M is the intracellular domain of gamma chain family cytokine receptor selected from IL2Ra, IL2Rb, IL4Ra, IL7Ra, IL9Ra, IL15Ra, IL21Ra; and N is the intracellular domain of IL2Rg.

For further optimizing the method of preparing the aforesaid CAR-T cell, the technical means used in the present invention further includes:

further, the construction of lentiviral vector and production of virus include: forming a fusion protein of scFv(X)-(Y)CD3zeta, M and N by overlap PCR, and adding restriction sites to both ends of the fusion protein to clone a lentiviral vector; subjecting the clones sequenced correctly to a large scale endotoxin-free extraction, and co-transfecting with a lentiviral packaging plasmid; after a predetermined period of time, collecting the supernatant, filtering, centrifuging to concentrate the virus, to obtain the scFv(X)-(Y)CD3zeta-MN virus.

Still further, said construction of lentiviral vector and production of virus are as follows: forming a fusion protein of scFv(X)-(Y)CD3zeta, M and N by overlap PCR, adding EcoRI and BamHI restriction sites to both ends of the fusion protein to clone the pCDH-MSCVEF vector; subjecting the clones sequenced correctly to a large scale endotoxin-free extraction, and co-transfecting with lentiviral packaging plasmid into 293X; after 48 and 72 hours, collecting the supernatant, filtering it with a 0.45 uM filter and centrifuging at 25000 RPM for 2 hours to concentrate the viruses to obtain the scFv(X)-(Y)CD3zeta-MN virus.

Further, the specific steps of preparing the scFv(X)-(Y)CD3zeta-MN CAR-T cell include: isolating human PBMC for purification, inoculating into a culture plate under suitable stimulation conditions, culturing for a predetermined time period, infecting with the scFv(X)-(Y)CD3zeta-MN virus obtained in Step 1, and subjecting to cell expansion under suitable stimulation conditions. After 2 rounds of expansion under stimulation, the obtained cells are the scFv(X)-(Y)CD3zeta-MN CAR-T cells.

Further, the stimulation conditions for culturing the isolated and purified human PBMC are anti-hCD3 and anti-hCD28; and the stimulation conditions for cell expansion are stimulation by use of artificial antigen presenting cell or anti-hCD3/28 every 6 days.

Still further, said specific steps of preparing the scFv(X)-(Y)CD3zeta-MN CAR-T cell are as follows: purifying human PBMC with a Stemcell T cell isolation kit, inoculating into a 96-well culture plate coated by anti-hCD3 and anti-hCD28. After 2 days, infecting the scFv(X)-(Y)CD3zeta-MN virus obtained in Step 1 at MOI=10-20. After 1 day, continuing to culture cells with the medium changed, and stimulating with artificial antigen presenting cell or anti-hCD3/28 every 6 days. After 2 rounds of stimulation, the obtained cells are scFv(X)-(Y)CD3zeta-MN CAR-T.

Further, said X is selected from anti-CD19 antibody, anti-CD20 antibody, EGFR antibody, HER2 antibody, EGFRVIII antibody.

Further, said X is anti-CD20 antibody, said Y is 4-1BB, and said M is one selected from IL2Rb, IL4Ra, IL7Ra, IL9Ra, IL21Ra.

Further, said scFv(X)-(Y)CD3zeta is scFv-antihCD20-20BBZ with a sequence as set forth in SEQ ID No.1; said intracellular domain of IL7Ra has a sequence as set forth in SEQ ID No. 2; said intracellular domain of IL2Rb has a sequence as set forth in SEQ ID No. 3; said intracellular domain of IL4Ra has a sequence as set forth in SEQ ID No. 4; said intracellular domain of IL9Ra has a sequence as set forth in SEQ ID No. 5; said intracellular domain of IL21Ra has a sequence as set forth in SEQ ID No. 6; and said intracellular domain of IL2Rg has a sequence as set forth in SEQ ID No. 7.

Further, said lentiviral packaging plasmid in Step 1 includes VSV-g, pMD Gag/Pol, RSV-REV, and the centrifuging is performed with Beckman ultracentrifuge and SW28 head.

A fifth object of the present invention is to provide a formulation including the aforesaid CAR-T cell or the CAR-T cell prepared by the aforesaid preparation method. Further, said formulation further includes a pharmaceutically diluents or excipient.

A sixth object of the present invention is to provide use of the aforesaid chimeric antigen receptor, the aforesaid CAR-T cell or the CAR-T cell prepared by the aforesaid preparation method in the preparation of a medicament for treating or preventing tumors.

Further, said tumors are solid tumors. Examples of the solid tumors include, but are not limited to, lymphoma, renal tumor, neuroblastoma, germ cell tumor, osteosarcoma, chondrosarcoma, soft tissue sarcoma, liver tumor, thymoma, pulmonary blastoma, pancreatoblastoma, hemangioma, etc.

As compared with the prior art, the present invention has the following beneficial effects:

said CAR-T cell of the present invention significantly increases the tumor killing ability and the expansion ability, and has significantly increased ability of killing solid/metastatic tumors. Said CAR-T cell of present invention includes a third signal receptor (IL2Ra, IL2Rb, IL4Ra, IL7Ra, IL9Ra, IL15Ra, IL21Ra, etc.), which is not a conventionally used ligand or excreted factor. For example, the third signal receptor IL7Ra is primarily expressed in memory CD4 and CD8 T cells, and plays an important role in the long-term survival of T cells and the formation of memory T cells. Integrating the third signal receptor signal into the CAR-T has a potential effect-enhancing function, and only works on the CAR-T cell, thereby reducing the risk of causing an immune side effect.

The present invention constructs a novel CAR-T cell including the third signal receptor, which increases the activation ability and survival ability of CAR-T cells in tumors as compared with the current CAR-T technology in clinic use. The activation ability and expansion ability of the cells are significantly enhanced, so that the CAR-T cell exhibits increased therapeutic effects and has more superior anti-tumor therapeutic effect.

DETAILED DESCRIPTION OF THE EMBODIMENTS

The present invention provides a chimeric antigen receptor including a third signal receptor, and said chimeric antigen receptor have a structure of scFv(X)-(Y)CD3zeta-MN; wherein X is a tumor-targeting antibody or other protein; Y is the intracellular domain of costimulatory receptor, said costimulatory receptor is selected from ICOS, CD28, CD27, HVEM, LIGHT, CD40L, 4-1BB, OX40, DR3, GITR, CD30, TIM1, SLAM, CD2, CD226; M is the intracellular domain of gamma chain family cytokine receptor, said cytokine receptor is selected from IL2Ra, IL2Rb, IL4Ra, IL7Ra, IL9Ra, IL15Ra, IL21Ra; and N is the intracellular domain of IL2Rg. The present invention also relates to a CAR-T cell constructed with a recombinant expression vector of any one of the aforesaid chimeric antigen receptor and a preparation method therefor, a formulation including the CAR-T cell, and use of the CAR-T cell.

Hereinafter the embodiments of the present invention are further described with reference to the accompanying drawings and examples. The following examples are only for more clearly illustrating the technical solutions of the present invention, but not for limiting the protective scope of the present invention.

Figure 1:
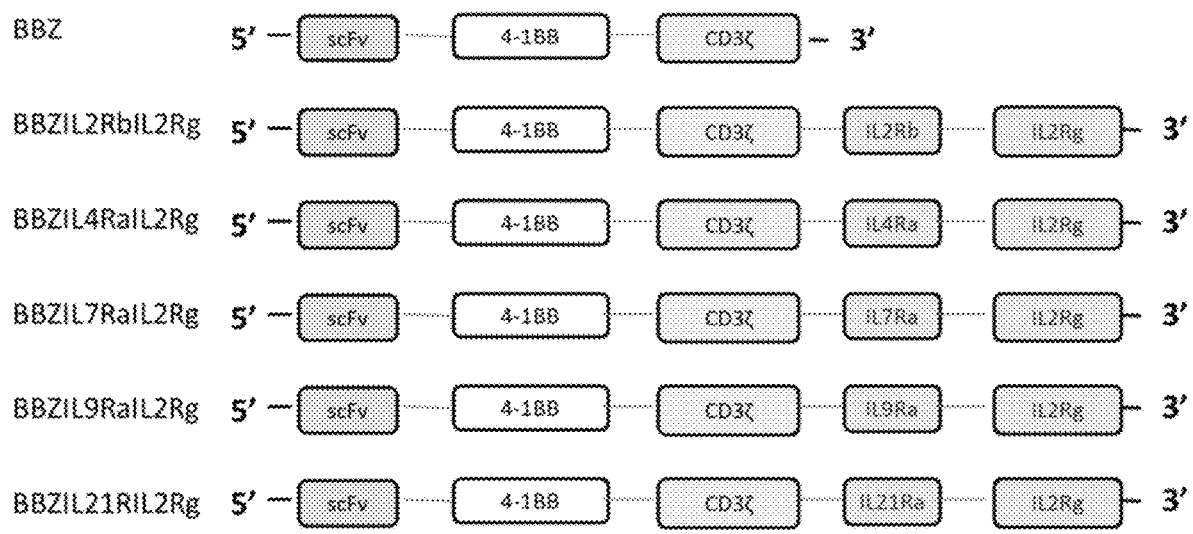
FIG. 1 is an illustrative schematic view showing the molecular structure of chimeric antigen receptor (CAR) including a third signal receptor in embodiments of the present invention.

The chimeric antigen receptors (CAR) including the third signal receptor used in the examples of the present invention are BBZIL2RbIL2Rg, BBZIL4RaIL2Rg, BBZIL7RaIL2Rg, BBZIL9RaIL2Rg, BBZIL21RaIL2Rg, respectively, and their structures are shown in FIG. 1.

Example 1—Preparation of 20BBZIL2RbIL2Rg CAR-T Cell

Figure 2:
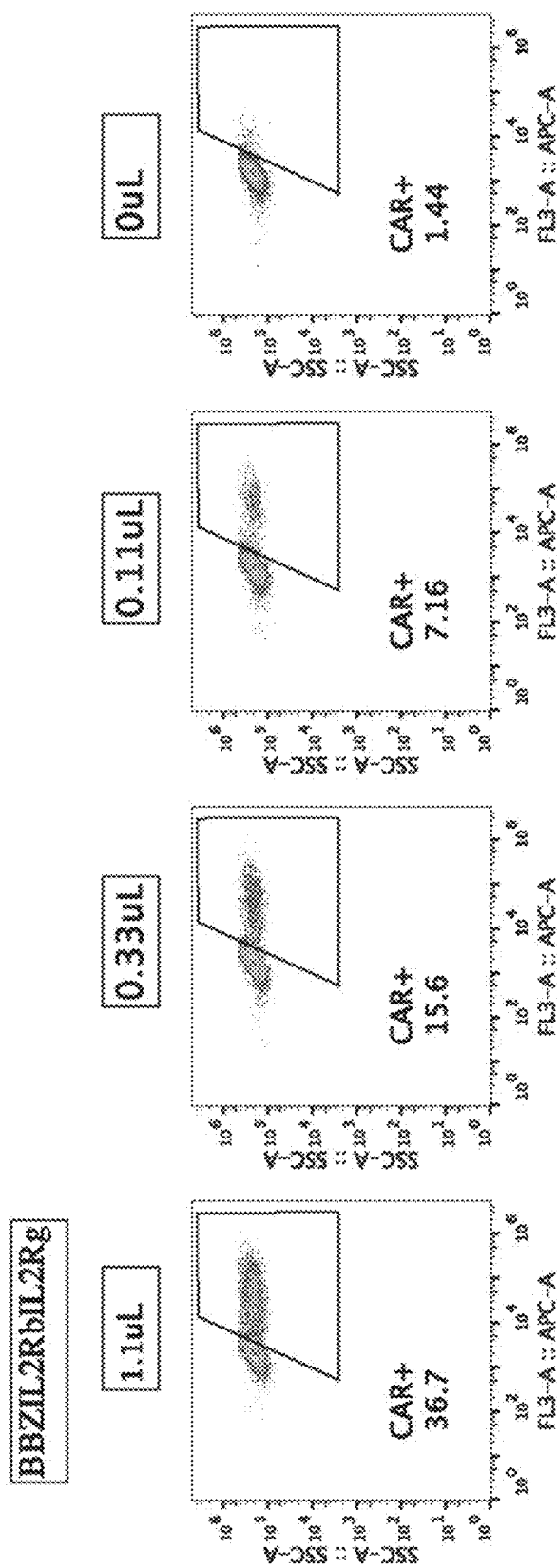
FIG. 2 is a schematic view showing the virus titer measured after 293 cells were infected with BBZIL2RbIL2Rg virus in an embodiment of the present invention.

The preparation of said 20BBZIL2RbIL2Rg CAR-T cell in this example includes the following steps:

1. Construction of Lentiviral Vector pCDH-MSCVEF-20BBZIL2RbIL2Rg and Production of Virus Forming a fusion protein of scFv-antihCD20-20BBZ (SEQ ID No.1), IL2Rb intracellular domain (SEQ ID No.3) and the intracellular domain of IL2Rg (SEQ ID No.7) by overlap PCR, and adding EcoRI and BamHI restriction sites to both ends of the fusion protein to clone a pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it with a 0.45 uM filter, and centrifuging with Beckman ultracentrifuge and SW28 head at 25000RPM for 2 hours to concentrate the virus, that is, the pCDH-MSCVEF-20BBZIL2RbIL2Rg virus (briefly, 20BBZIL2RbIL2Rg virus) for use in the subsequent production of CAR-T cells. Meanwhile, producing the control pCDH-MSCVEF-20BBZ virus (briefly, 20BBZ virus), and infecting 293 cells with the obtained 20BBZIL2RbIL2Rg virus to determine the virus titer, as shown in FIG. 2.

2. Preparation of 20BBZIL2RbIL2Rg CAR-T Cell and 20BBZ CAR-T Cell

Figure 7:
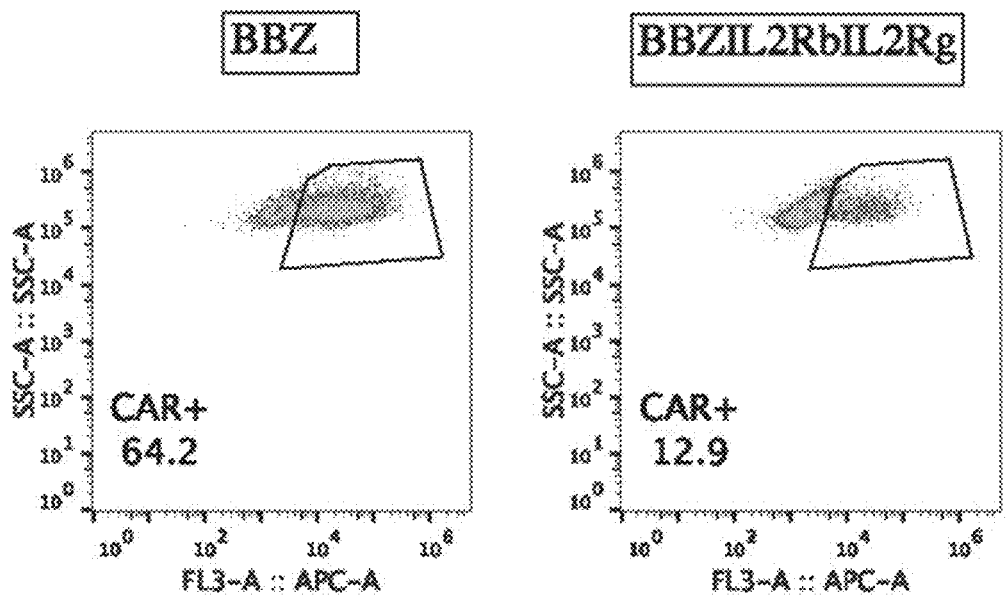
FIG. 7 is a schematic view showing the results of phenotypic analysis of BBZ CAR-T cell and BBZIL2RbIL2Rg CAR-T cell in an embodiment of the present invention.

Purifying human PBMC with a Stemcell T cell isolation kit, inoculating into a 96-well culture plate coated by anti-hCD3 and anti-hCD28. After 2 days, infecting the cells with 20BBZ virus and 20BBZIL2RbIL2Rg virus at MOI=10-20. After 1 day, continuing to culture the cells with the medium changed, and stimulating with artificial antigen presenting cell or anti-hCD3/28 every 6 days. After 2 rounds of stimulation, the obtained cells are 20BBZ CAR-T cell and 20BBZIL2RbIL2Rg CAR-T cell for use in the subsequent experiments and phenotypic analysis. As shown in FIG. 7, the obtained cells are CAR-positive.

Example 2—Preparation of 20BBZIL4RaIL2Rg CAR-T Cell

Figure 3:
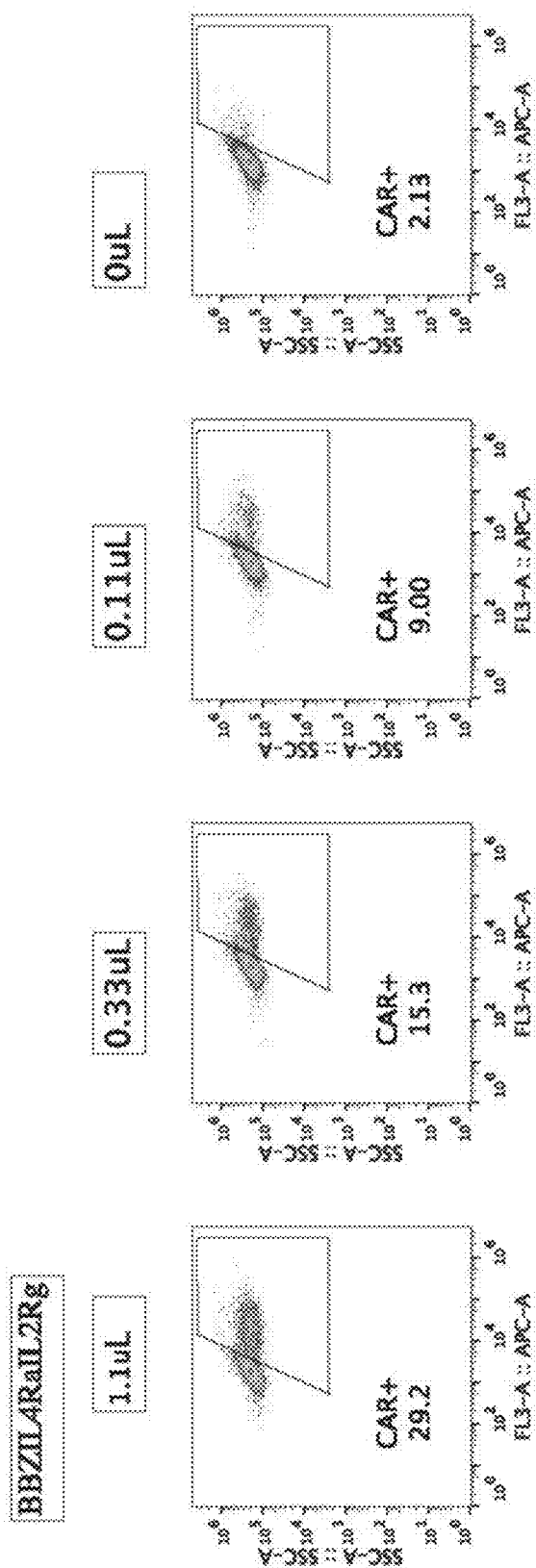
FIG. 3 is a schematic view showing the virus titer measured after 293 cells were infected with BBZIL4RaIL2Rg virus in an embodiment of the present invention.

The preparation of said 20BBZIL4RaIL2Rg CAR-T cell in this example includes the following steps:

1. Construction of lentiviral vector pCDH-MSCVEF-20BBZIL4RaIL2Rg and production of virus Forming a fusion protein of scFv-antihCD20-20BBZ (SEQ ID No.1), IL4Ra intracellular domain (SEQ ID No.4) and the intracellular domain of IL2Rg (SEQ ID No.7) by overlap PCR, and adding EcoRI and BamHI restriction sites to both ends of the fusion protein to clone a pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it with a 0.45 uM filter, and centrifuging with Beckman ultracentrifuge and SW28 head at 25000RPM for 2 hours to concentrate the viruses, that is, the pCDH-MSCVEF-20BBZIL4RaIL2Rg virus (briefly, 20BBZIL4RaIL2Rg virus) for use in the subsequent production of CAR-T cells. Meanwhile, producing the control pCDH-MSCVEF-20BBZ virus (briefly, 20BBZ virus), and infecting 293 cells with the obtained 20BBZIL4RaIL2Rg virus to determine the virus titer, as shown in FIG. 3.

2. Preparation of 20BBZIL4RaIL2Rg CAR-T Cell and 20BBZ CAR-T Cell

Figure 8:
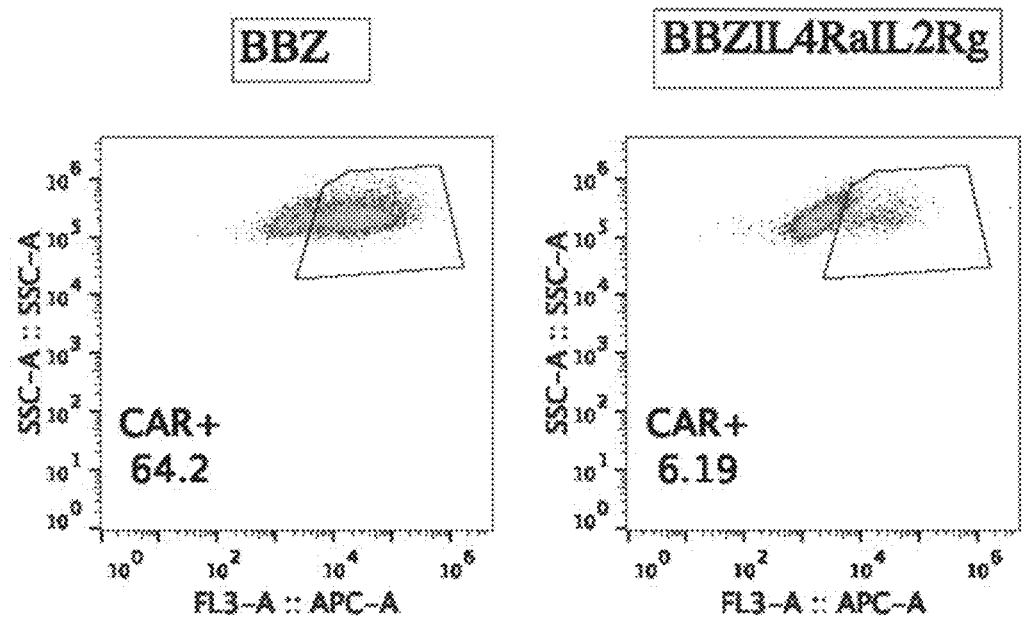
FIG. 8 is a schematic view showing the results of phenotypic analysis of BBZ CAR-T cell and BBZIL4RaIL2Rg CAR-T cell in an embodiment of the present invention.

Purifying human PBMC with a Stemcell T cell isolation kit, inoculating into a 96-well culture plate coated by anti-hCD3 and anti-hCD28. After 2 days, infecting the cells with 20BBZ virus and 20BBZIL4RaIL2Rg virus at MOI=10-20. After 1 day, continuing to culture the cells with the medium changed, and stimulated by artificial antigen presenting cell or anti-hCD3/28 every 6 days. After 2 rounds of stimulation, the obtained cells are 20BBZCAR-T cell and 20BBZIL4RaIL2RgCAR-T cell for use in the subsequent experiments and phenotypic analysis. As shown in FIG. 8, the obtained cells are CAR-positive.

Example 3—Preparation of 20BBZIL7RaIL2Rg CAR-T Cell

Figure 4:
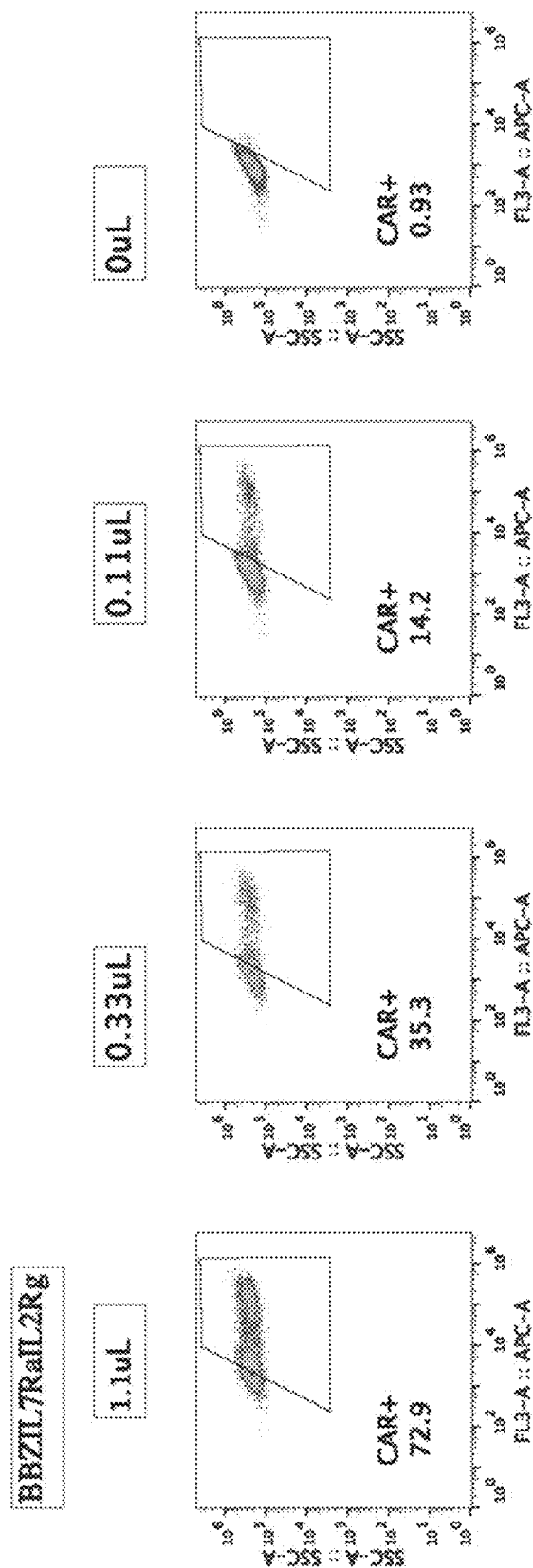
FIG. 4 is a schematic view showing the virus titer measured after 293 cells were infected with BBZIL7RaIL2Rg virus in an embodiment of the present invention.

The preparation of said 20BBZIL7RaIL2Rg CAR-T cell in this example includes the following steps:

1. Construction of Lentiviral Vector pCDH-MSCVEF-20BBZIL7RaIL2Rg and Production of Virus Forming a fusion protein of scFv-antihCD20-20BBZ (SEQ ID No.1), IL7Ra intracellular domain (SEQ ID No.2) and the intracellular domain of IL2Rg (SEQ ID No.7) by overlap PCR, and adding EcoRI and BamHI restriction sites to both ends of the fusion protein to clone a pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it with a 0.45 uM filter, and centrifuged with Beckman ultracentrifuge and SW28 head at 25000RPM for 2 hours to concentrate the viruses, that is, the pCDH-MSCVEF-20BBZIL7RaIL2Rg virus (briefly, 20BBZIL7RaIL2Rg virus) for use in the subsequent production of CAR-T cells. Meanwhile, producing the control pCDH-MSCVEF-20BBZ virus (briefly, 20BBZ virus), and infecting 293 cells with 20BBZIL7RaIL2Rg virus to determine the virus titer, as shown in FIG. 4.

2. Preparation of 20BBZIL7RaIL2Rg CAR-T Cell and 20BBZ CAR-T Cell

Figure 9:
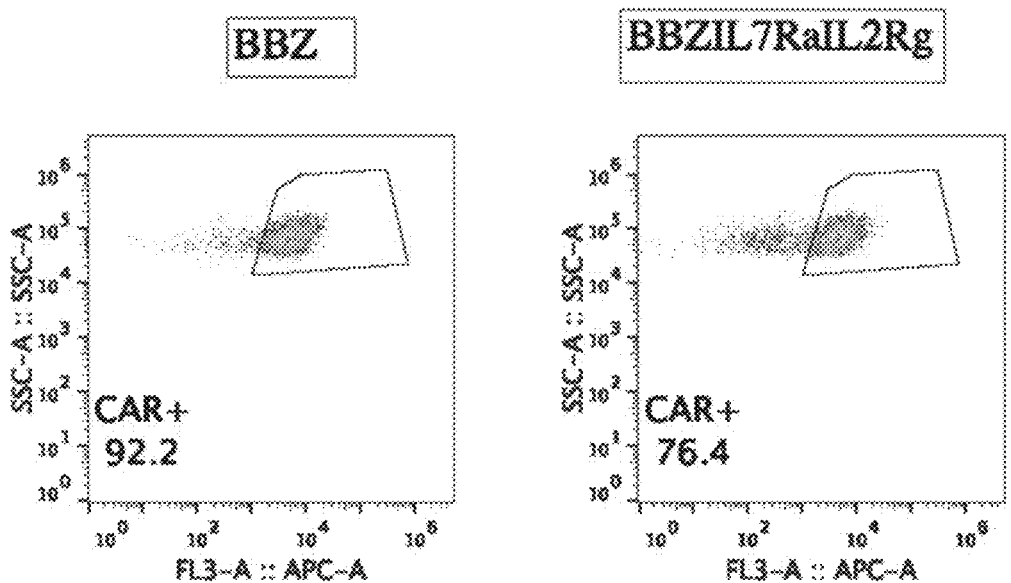
FIG. 9 is a schematic view showing the results of phenotypic analysis of BBZ CAR-T cell and BBZIL7RaIL2Rg CAR-T cell in an embodiment of the present invention.

Purifying human PBMC with a Stemcell T cell isolation kit, inoculating into a 96-well culture plate coated by anti-hCD3 and anti-hCD28. After 2 days, infecting the cells with 20BBZ virus and 20BBZIL7RaIL2Rg virus at MOI=10-20. After 1 day, continuing to culture the cells with the medium changed, and stimulating with artificial antigen presenting cell or anti-hCD3/28 every 6 days. After 2 rounds of stimulation, the obtained cells are 20BBZCAR-T cell and 20BBZIL7RaIL2RgCAR-T cell for use in the subsequent experiments and phenotypic analysis. As shown in FIG. 9, the obtained cells are CAR-positive.

Example 4—Preparation of 20BBZIL9RaIL2Rg CAR-T Cell

Figure 5:
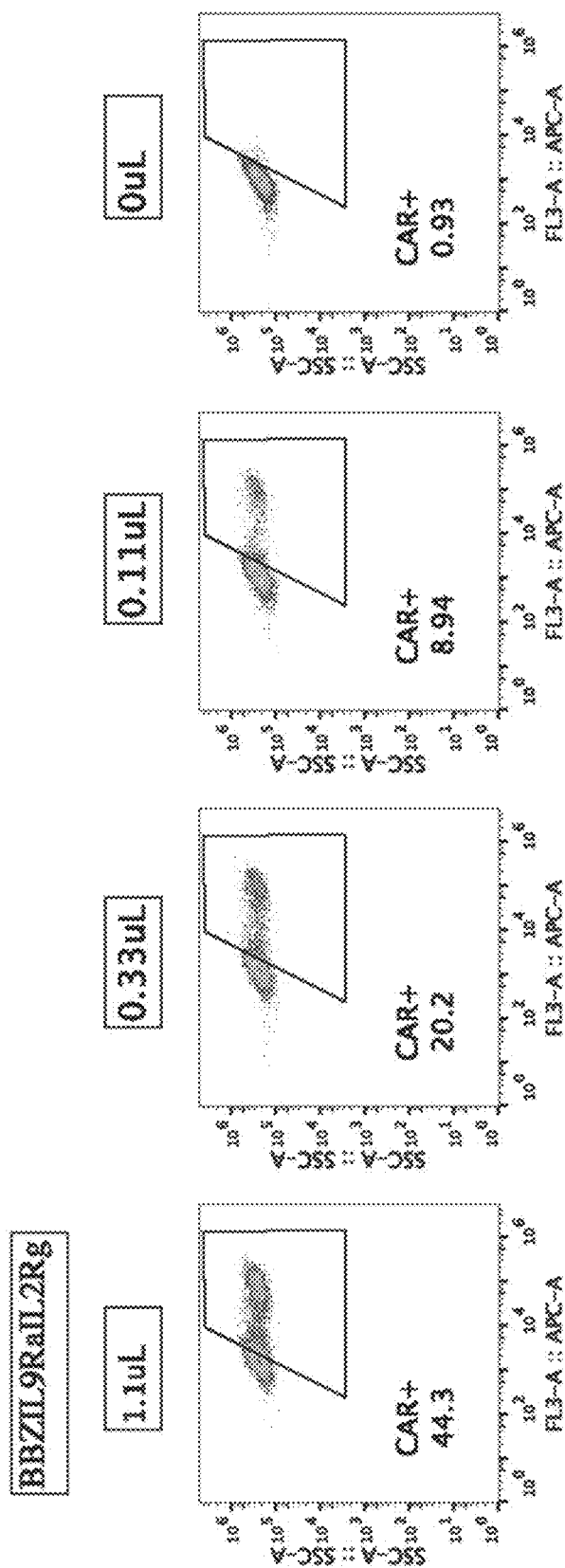
FIG. 5 is a schematic view showing the virus titer measured after 293 cells were infected with BBZIL9RaIL2Rg virus in an embodiment of the present invention.

The preparation of said 20BBZIL9RaIL2Rg CAR-T cell in this example includes the following steps:

1. Construction of Lentiviral Vector pCDH-MSCVEF-20BBZIL9RaIL2Rg and Production of Virus Forming a fusion protein of scFv-antihCD20-20BBZ (SEQ ID No.1), IL9Ra intracellular domain (SEQ ID No.5) and the intracellular domain of IL2Rg (SEQ ID No.7) by overlap PCR, and adding EcoRI and BamHI restriction sites to both ends of the fusion protein to clone a pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it with a 0.45 uM filter, and centrifuging with Beckman ultracentrifuge and SW28 head at 25000RPM for 2 hours to concentrate the viruses, that is, the pCDH-MSCVEF-20BBZIL9RaIL2Rg virus (briefly, 20BBZIL9RaIL2Rg virus) for use in the subsequent production of CAR-T cells. Meanwhile, producing the control pCDH-MSCVEF-20BBZ virus (briefly, 20BBZ virus), and infecting 293 cells with 20BBZIL9RaIL2Rg virus to determine the virus titer, as shown in FIG. 5.

2. Preparation of 20BBZIL9RaIL2Rg CAR-T Cell and 20BBZ CAR-T Cell

Figure 10:
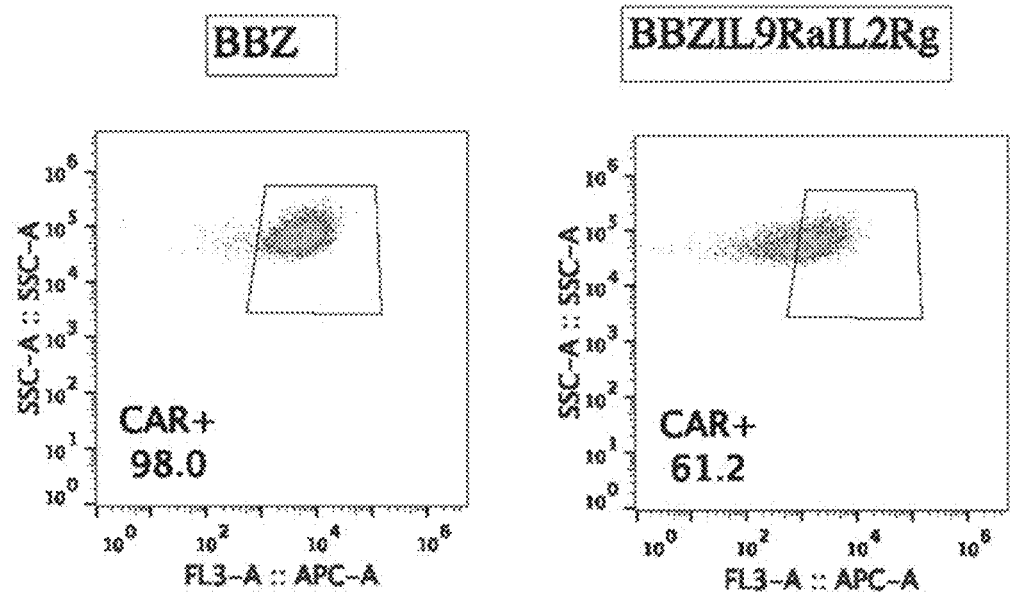
FIG. 10 is a schematic view showing the results of phenotypic analysis of BBZ CAR-T cell and BBZIL9RaIL2Rg CAR-T cell in an embodiment of the present invention.

Purifying human PBMC with a Stemcell T cell isolation kit, inoculating into a 96-well culture plate coated by anti-hCD3 and anti-hCD28. After 2 days, infecting the cells with 20BBZ virus and 20BBZIL9RaIL2Rg virus at MOI=10-20. After 1 day, continuing to culture the cells with the medium changed, and stimulating with artificial antigen presenting cell or anti-hCD3/28 every 6 days. After 2 rounds of stimulation, the obtained cells are 20BBZCAR-T cell and 20BBZIL9RaIL2RgCAR-T cell for use in the subsequent experiments and phenotypic analysis. As shown in FIG. 10, the obtained cells are CAR-positive.

Example 5—Preparation of 20BBZIL21RaIL2Rg CAR-T Cell

Figure 6:
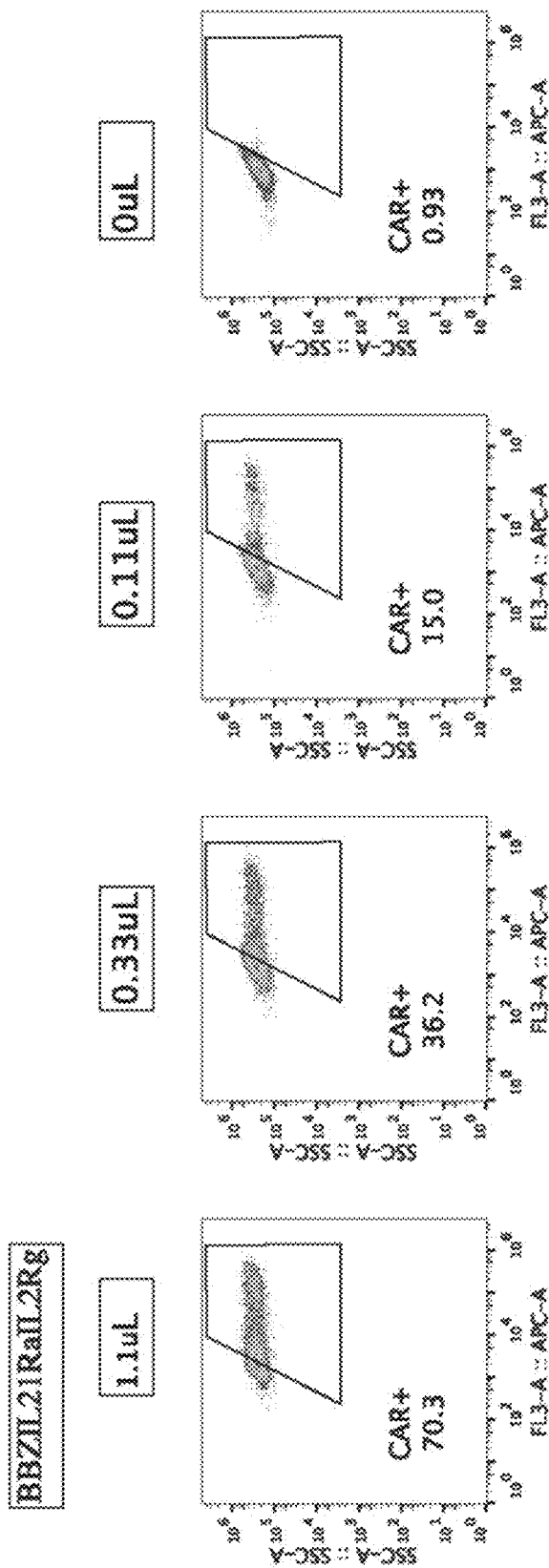
FIG. 6 is a schematic view showing the virus titer measured after 293 cells were infected with BBZIL21RaIL2Rg virus in an embodiment of the present invention.

The preparation of the 20BBZIL21RaIL2Rg CAR-T cell in this example includes the following steps:

1. Construction of Lentiviral Vector pCDH-MSCVEF-20BBZIL21RaIL2Rg and Production of Virus Forming a fusion protein of scFv-antihCD20-20BBZ (SEQ ID No.1), IL21Ra intracellular domain (SEQ ID No.6) and the intracellular domain of IL2Rg (SEQ ID No.7) by overlap PCR, and adding EcoRI and BamHI restriction sites to both ends of the fusion protein to clone a pCDH-MSCVEF vector. Subjecting the clones sequenced correctly to a large scale endotoxin-free extraction, and co-transfecting with lentiviral packaging plasmid (VSV-g, pMD Gag/Pol, RSV-REV) into 293X. After 48 and 72 hours, collecting the supernatant, filtering it with a 0.45 uM filter, and centrifuging with Beckman ultracentrifuge and SW28 head at 25000RPM for 2 hours to concentrate the viruses, that is, the pCDH-MSCVEF-20BBZIL21RaIL2Rg virus (briefly, 20BBZIL21RaIL2Rg virus) for use in the subsequent production of CAR-T cells. Meanwhile, producing the control pCDH-MSCVEF-20BBZ virus (briefly, 20BBZ virus), and infecting 293 cells with 20BBZIL21RaIL2Rg virus to determine the virus titer, as shown in FIG. 6.

2. Preparation of 20BBZIL21RaIL2Rg CAR-T Cell and 20BBZ CAR-T Cell

Figure 11:
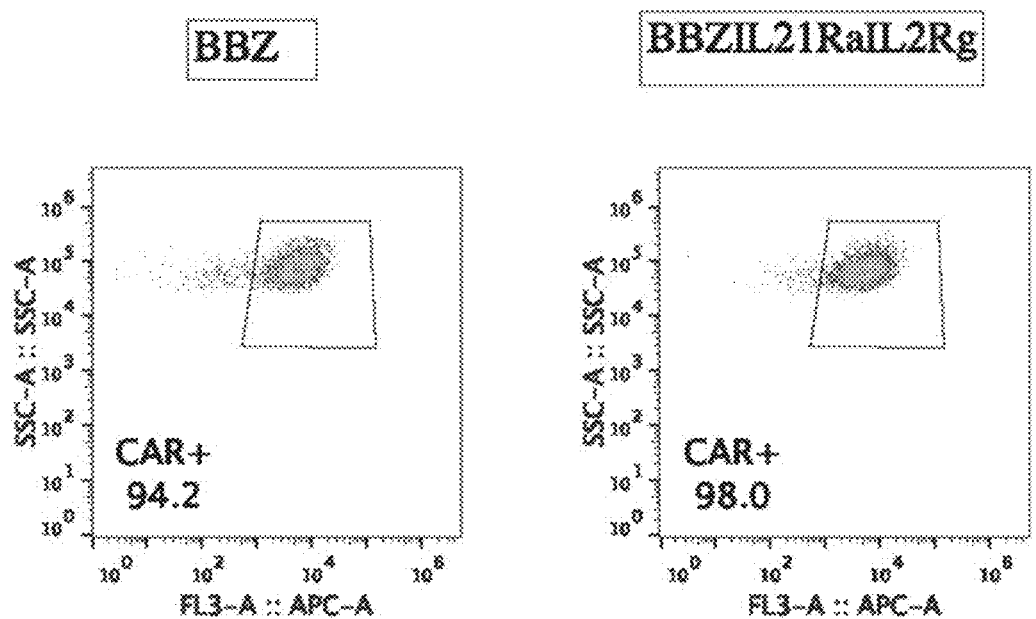
FIG. 11 is a schematic view showing the results of phenotypic analysis of BBZ CAR-T cell and BBZIL21RaIL2Rg CAR-T cell in an embodiment of the present invention.

Purifying human PBMC with a Stemcell T cell isolation kit, inoculating into a 96-well culture plate coated by anti-hCD3 and anti-hCD28. After 2 days, infecting the cells with 20BBZ virus and 20BBZIL21RaIL2Rg virus at MOI=10-20. After 1 day, continuing to culture the cells with the medium changed, and stimulating by artificial antigen presenting cell or anti-hCD3/28 every 6 days. After 2 rounds of stimulation, the obtained cells are 20BBZCAR-T cell and 20BBZIL21RaIL2RgCAR-T cell for use in the subsequent experiments and phenotypic analysis. As shown in FIG. 11, the obtained cells are CAR-positive.

Figure 12:
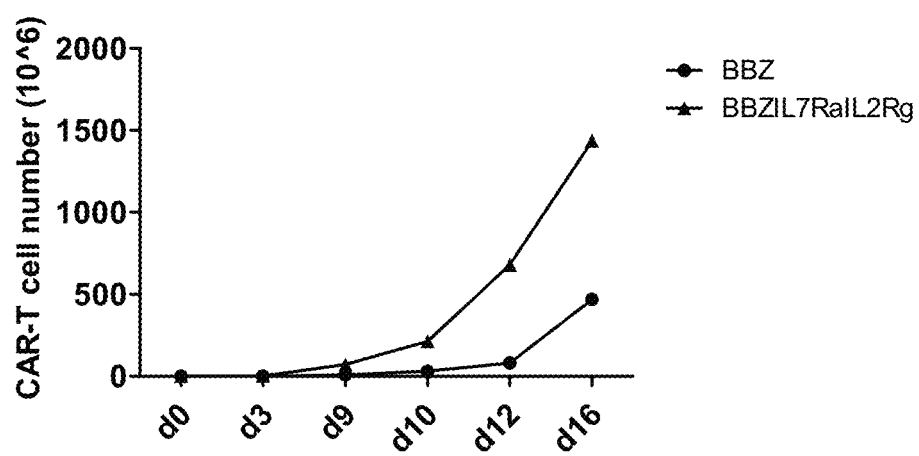
FIG. 12 is a schematic view showing the amplification ability of BBZ CAR-T cell and BBZIL7RaIL2Rg CAR-T cell in an embodiment of the present invention.

Example 6—Comparison of Expansion Abilities of 20BBZ CAR-T Cell and 20BBZIL7RaIL2Rg CAR-T Cell Culture the 20BBZ CAR-T cell and 20BBZIL7RaIL2Rg CAR-T cell prepared in Step 2 of Example 3 continuously for 14 days, and stimulate with artificial antigen presenting cell once every 6 days. Count the cells, and the results are shown in FIG. 12. It can be seen from the figure that 20BBZIL7RaIL2Rg CAR-T cell has enhanced proliferation ability as compared with 20BBZCAR-T cell.

Figure 13:
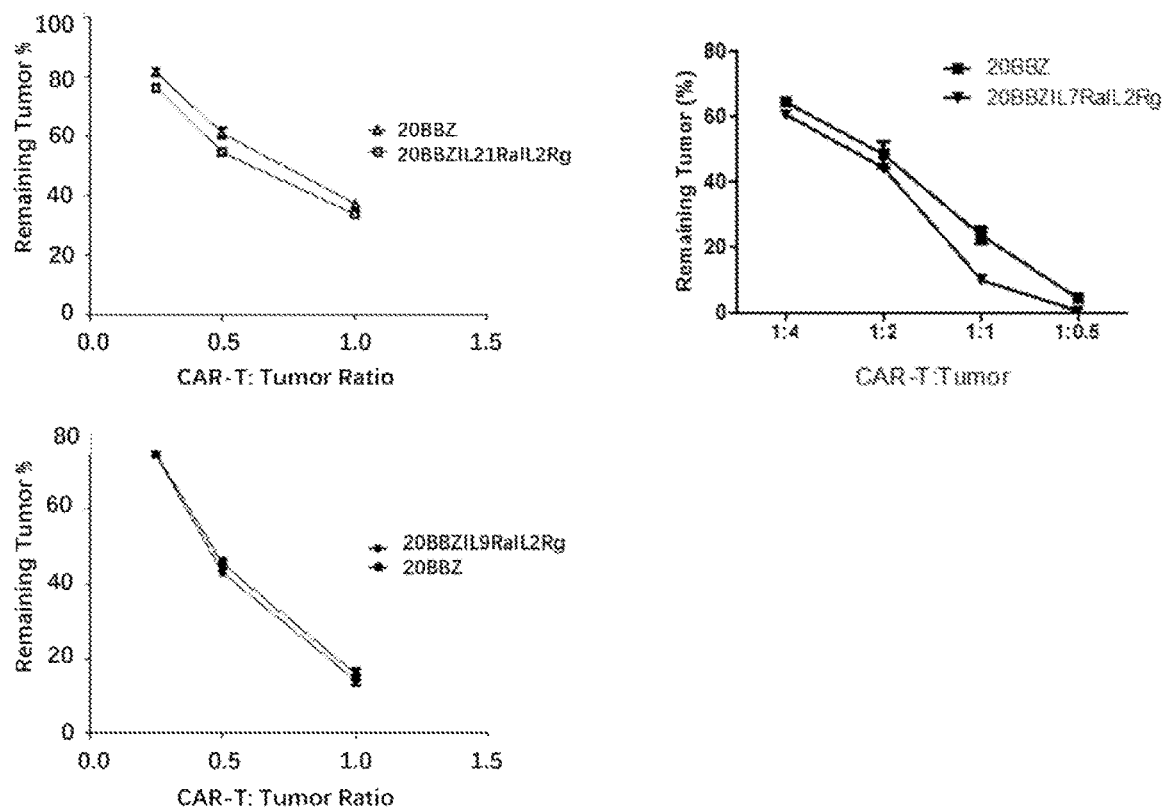
FIG. 13 is a schematic view showing the tumor killing ability of BBZ CAR-T cell and BBZIL7RaIL2Rg CAR-T cell in an embodiment of the present invention.

Example 7—Comparison of Tumor-Killing Abilities of 20BBZ CAR-T Cell and 20BBZIL7RaIL2Rg CAR-T Cell Inoculate the 20BBZ CAR-T cell and 20BBZIL7RaIL2Rg CAR-T cell prepared in Step 2 of Example 3 into a 96-well plate, and add the Raji tumor cells at a CAR-T:tumor cell ratio of 1:1, 1:2, 1:4. After 24 and 48 hours, compare the survival rates of tumor cells, and the results are shown in FIG. 13. It can be seen from the figure that the 20BBZIL7RaIL2Rg CAR-T cell has similar tumor killing ability as compared with 20BBZ CAR-T cell.

Figure 14:
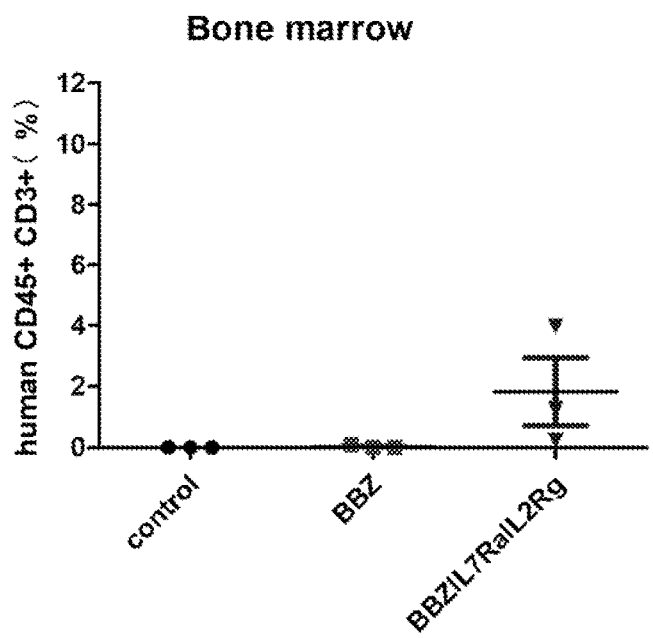
FIG. 14 is a schematic view showing the anti-tumor ability of BBZ CAR-T cell and BBZIL7RaIL2Rg CAR-T cell in an embodiment of the present invention.
Figure 15:
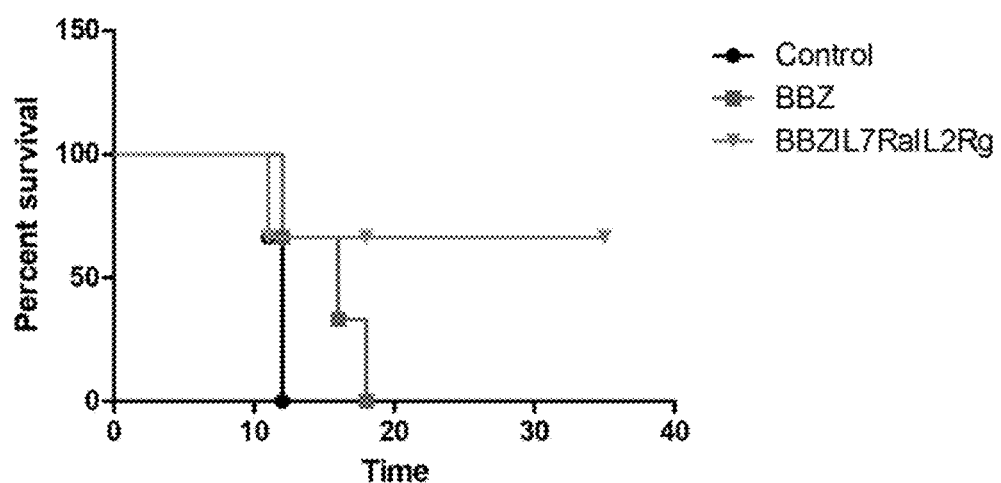
FIG. 15 is a schematic view showing the in vivo survival ability of BBZ CAR-T cell and BBZIL7RaIL2Rg CAR-T cell in an embodiment of the present invention.

Example 8—Comparison of Anti-Tumor Ability and In Vivo Survival Ability of 20BBZ CAR-T Cell and 20BBZIL7RaIL2Rg CAR-T Cell Inoculated $10^6$ Nalm-6 tumor cells intravenously into B-NDG mice. Treated the mice with $10^7$ 2 OBBZ CAR-T cells and 20BBZIL7RaIL2Rg CAR-T cells after 6 days. The mice were observed for their survival rates, and some mice were detected for the level of tumor cells and CAR-T cells in their marrow on Day 7. The results are shown in FIG. 14 and FIG. 15, respectively. It can be seen from the figures that 20BBZIL7RaIL2Rg CAR-T cell, as compared with 20BBZ CAR-T cell, substantially prolongs the survival of mice, and expanded more in vivo.

It can be seen from the aforesaid examples that the present invention constructs a novel CAR-T cells including a third signal receptor, which significantly increases the activation ability, survival ability, expansion ability of the CAR-T cells in tumors, as compared with the current CAR-T technology in clinic use, and has more superior anti-tumor therapeutic effect.

Hereinbefore the specific embodiments of the present invention are described in details. However, they are only used as examples, and the present invention is not limited to the specific embodiments as described above. For those skilled in the art, any equivalent modifications and substitutions made to the present invention are encompassed in the scope of the present invention. Therefore, all the equal transformations and modifications without departing from the spirit and scope of the present invention should be covered in the scope of the present invention.

What is claimed is:

1. A chimeric antigen receptor (CAR), wherein said chimeric antigen receptor has the structure of scFv(X)-(Y)CD3zeta-MN, wherein said scFv(X)-(Y)CD3zeta is scFv-antihCD20-20BBZ with a sequence as set forth in SEQ ID No.1; wherein M is an intracellular domain of IL7Ra, wherein the sequence of said intracellular domain of IL7Ra is as set forth in SEQ ID No.2; and N is an intracellular domain of IL2Rg, and the sequence of said intracellular domain of IL2Rg is as set forth in SEQ ID No.7.

2. A chimeric antigen receptor-T cell expressing the CAR of claim 1.

3. A chimeric antigen receptor-T cell comprising an expression vector encoding and expressing the CAR of claim 1.

4. A composition comprising the chimeric antigen receptor T cells of claim 2.

5. A method of treating a CD20 expressing tumor in vivo comprising administering an effective amount of the composition of claim 4.

6. A method of making a chimeric antigen receptor-T cell (CAR-T cell) expressing the chimeric antigen receptor of claim 1 comprising:

constructing a lentiviral vector comprising a nucleic acid encoding the chimeric antigen receptor of claim 1;

isolating human peripheral blood mononuclear cells and purifying T cells therefrom;

inoculating the purified T cells to a culture plate under suitable stimulation conditions;

culturing the culture plate for a predetermined period of time;

after the predetermined period of time infecting the T cells with the lentiviral vector encoding the chimeric antigen receptor and subjecting to infected cells to cell expansion under suitable stimulator conditions to obtain the CAR-T cell expressing the chimeric antigen receptor of claim 1.

* * * * *